United States Patent
Saalbach et al.

(10) Patent No.: US 12,354,721 B2
(45) Date of Patent: Jul. 8, 2025

(54) AUTOMATIC DIAGNOSIS REPORT PREPARATION (71) Applicant: KONINKLIJKE PHILIPS N.V., Eindhoven (NL)

(72) Inventors: Axel Saalbach, Hamburg (DE); Michael Grass, Buchholz in der Nordheide (DE); Tom Brosch, Hamburg (DE); Jens Von Berg, Hamburg (DE); Stewart Young, Hamburg (DE)

(73) Assignee: KONINKLIJKE PHLIPS N.V., Eindhoven (NL)

(*) Notice: Subject to any disclaimer, the term of this patent is extended or adjusted under 35 U.S.C. 154(b) by 913 days.

(21) Appl. No.: 16/959,223

(22) PCT Filed: Dec. 24, 2018

(86) PCT No.: PCT/EP2018/086839
§ 371 (c)(1),
(2) Date: Jun. 30, 2020

(87) PCT Pub. No.: WO2019/134872
PCT Pub. Date: Jul. 11, 2019

(65) Prior Publication Data
US 2020/0411150 A1  Dec. 31, 2020

(30) Foreign Application Priority Data
Jan. 2, 2018 (EP) ..................... 18150011

(51) Int. Cl.
*G16H 15/00* (2018.01)
*G06F 3/0482* (2013.01)
(Continued)

(52) U.S. Cl.
CPC ........... *G16H 15/00* (2018.01); *G06F 3/0482* (2013.01); *G06F 18/21* (2023.01); *G06F 18/24* (2023.01);
(Continued)

(58) Field of Classification Search
CPC ........ G16H 15/00; G16H 30/40; G16H 50/20; G06F 3/0482; G06F 40/274;
(Continued)

(56) References Cited

U.S. PATENT DOCUMENTS 9,177,110 B1  11/2015 Fram
2006/0190256 A1  8/2006 Stephanick
(Continued)

FOREIGN PATENT DOCUMENTS

JP  2009069893 A  4/2009
JP  2017010577 A  1/2017
WO  WO2017151757 A1  9/2017

OTHER PUBLICATIONS

PCT International Search Report, International Application No. PCT/EP2018/084890, Mar. 25, 2019.
(Continued)

*Primary Examiner* — Hien L Duong (57) ABSTRACT

In a conventional system for preparing reports on findings in medical images, the actual formulation of the report is not or only insufficiently supported by the computer-based system. Although there are efforts to improve such a system through automatic reporting, however, in previous systems, the error rate is too high and/or the operation of the system too complicated. This application proposes to provide text prediction to a user on the display device. The text prediction is based on prior analyzing the image content of a medical image at is displayed to the user at least when the user activates a text field shown on the display device via the
(Continued)

input unit. The displayed text prediction is selected from a pre-defined set of text modules that are associated to the analysis result.

19 Claims, 5 Drawing Sheets

(51) Int. Cl.
| | |
|---|---|
| *G06F 18/21* | (2023.01) |
| *G06F 18/24* | (2023.01) |
| *G06F 40/274* | (2020.01) |
| *G06N 20/00* | (2019.01) |
| *G06T 7/00* | (2017.01) |
| *G16H 30/40* | (2018.01) |
| *G16H 50/20* | (2018.01) |
| *G06N 3/04* | (2023.01) |

(52) U.S. Cl.
CPC ........... *G06F 40/274* (2020.01); *G06N 20/00* (2019.01); *G06T 7/0012* (2013.01); *G16H 30/40* (2018.01); *G16H 50/20* (2018.01); *G06N 3/04* (2013.01); *G06T 2200/24* (2013.01); *G06T 2207/20081* (2013.01); *G06T 2207/30004* (2013.01)

(58) Field of Classification Search
CPC .... G06K 9/6217; G06K 9/6267; G06N 20/00; G06N 3/04; G06T 7/0012; G06T 2200/24; G06T 2207/20081; G06T 2207/30004
See application file for complete search history.

(56) References Cited

U.S. PATENT DOCUMENTS

| | | |
|---|---|---|
| 2006/0274928 A1 | 12/2006 | Collins |
| 2009/0171871 A1 | 7/2009 | Zhang |
| 2009/0297013 A1 | 12/2009 | Chaudhuri |
| 2011/0225114 A1* | 9/2011 | Gotthardt ............... G16H 10/20 706/50 |
| 2013/0132119 A1 | 5/2013 | Imam |
| 2015/0186538 A1* | 7/2015 | Yan ..................... G06F 16/9535 707/722 |
| 2016/0350484 A1* | 12/2016 | Son ........................ G16H 10/60 |
| 2016/0350919 A1 | 12/2016 | Steigauf |
| 2017/0091413 A1* | 3/2017 | Kondo ................... G16H 70/60 |
| 2017/0140008 A1* | 5/2017 | Ramaswami ......... G06F 16/248 |
| 2017/0192991 A1* | 7/2017 | Touma ................ G06F 16/3322 |
| 2019/0150857 A1* | 5/2019 | Nye ...................... G16H 50/20 |

OTHER PUBLICATIONS

Vinyals O. et al., "Show and Tell: A Neural Image Caption Generator", Abstract, Computer Science > Computer Vision and Pattern Recognition, Oct. 20, 2017.

* cited by examiner

AUTOMATIC DIAGNOSIS REPORT PREPARATION

FIELD OF THE INVENTION

The present invention relates to computer-aided diagnosis report preparation or creation, which is based on automatic evaluation of medical images. In particular, a system for computer-aided diagnosis report preparation is discussed, as well as an associated method, a computer program element, and a computer readable medium.

BACKGROUND OF THE INVENTION

Reporting findings from observations or abnormalities discovered in medical, in particular radiological images represents a significant amount of effort in diagnostic radiology, and requires time and thereby causes costs. These reports must also be recorded in writing and/or digitally and are usually part of the patient's record. Recently, the automatic analysis of such images by electronic image processing methods has made progress. However, this has not or hardly improved the reporting, i.e. the procedure for creating a report. Accordingly, today dictation and speech recognition are still widely used by radiologists for reporting. To reduce the time and/or costs required, suggestions have already been made.

US patent application US 2009/0171871 A1 discloses computer-aided detection, review and diagnosis by utilizing different learning methods. A fuzzy system is used for mapping the findings to diagnostic reports constructed using a formal language.

Further, US patent application US 2006/0274928 A1 discusses a system for automatic analyzing medical images and computing a diagnosis. Upon selecting a diagnosis by a user, a diagnosis report is generated electronically.

Furthermore, in US patent application US 2016/0350919 A1 a deep learning model is selected for automated image recognition of a particular medical condition on image data, and applied to the image data to recognize characteristics of the particular medical condition. For reporting, in a graphical user interface, report content can be pre-selected.

Furthermore, in US patent U.S. Pat. No. 9,177,110 B1 various systems and methods for improved report interaction and generation are described.

Furthermore, US patent application US 2006/0190256 A1 describes a digital processing device that receives inherently ambiguous user input wherein the device interprets the received user input against a vocabulary to yield candidates such as words.

Such approaches can, however, be further improved.

SUMMARY OF THE INVENTION

It is an object of the present invention to provide an improved, in particular a more efficient way of providing computer-aided diagnosis report preparation. The object of the present invention is solved by the subject-matter of the appended independent claims, wherein further embodiments are incorporated in the dependent claims.

According to a first aspect of the present invention, there is provided a system for computer-aided diagnosis report preparation or creation, wherein the reporting preparation is based on automatic evaluation of medical image data provided by medical or, in particular radiologic, imaging, such as X-ray, computed tomography, magnetic resonance imaging, sonography etc. Accordingly, the system is in particular adapted to assist a radiologist or other physician electronically in preparing or creating a report on e.g. observations or abnormalities that have been discovered by evaluating the images.

The system comprises:

An image processing unit adapted to read out at least image content from the provided image data.

After creating one or more images by one of the exemplary listed imaging methods above and, preferably, providing them to a healthcare management system, these are processed and/or analyzed electronically by means of computer-aided image processing, wherein handcrafted image analysis features or deep learning algorithms can be used.

In this description, a system unit like the image processing unit may generally be understood as part of a controller, such as a software program, a part of a software program or a software module, or a correspondingly configured electronic circuit, such as a graphics processer or card, or the like. Although in this description a functional designation of the units is used, this does not necessarily imply that they are individual, separate units. Rather, several of the functionalities can be summarized in a system unit.

An image analyzing unit adapted to analyze the read-out image content based on pre-defined or trained characteristics and to derive analysis results from the analyzed image content.

In other words, the image analyzing unit may be capable to detect characteristics of e.g. medical abnormalities or observations, such as indicators for diseases, in the read-out image content. As a result, it may determine at least one possible disease that is at least derived from the read-out image content. Additionally, meta-data may be read-out from the images and may also be analyzed.

During or after image processing, report-relevant characteristics, in particular optically detectable observations and/or abnormalities which may indicate a possible disease can be determined by image analyzing or, in particular, by disease detection algorithms using handcrafted image features or methods, computer vision techniques or deep learning algorithms. For example, benign or malignant tumor characterization, pulmonary embolism detection etc. can be performed.

A display device that has, or is adapted to display, at least one text field for displaying written text, text prompts etc. to a user, such as a radiologist or other physician.

The text field may constitute or may be a part of a graphic user interface that represents a reporting mask. Ideally, it is displayed adjacent to one or more of the processed and/or analyzed images so that the radiologist can review the image or series of images while writing the report.

An input unit for interacting with the user to at least activate the text field.

For example, the input unit may be a keyboard, a touch pad, a voice input engine including a microphone etc. In the simplest case, the report is created by typing text via a conventional computer keyboard.

A text generating unit that is adapted to provide text prediction, e.g. visual display of text suggestions that are individually selectable, to a user on the display device, at least when the user activates the text field via the input unit, wherein the text prediction is selected from a pre-defined set of text modules that are associated to the analysis result.

In this description, text prediction can be understood as visual display of text suggestions that are individually selectable at runtime or during text input, respectively. Generally, the text suggestions depend on the situation and/or the context. The text suggestions may contain single words, phrases, complete sentences etc., in particular established medical terms or phrases, such as descriptions of findings, recommended therapies, follow-up exams etc. Preferably, the respective suggestion is directly derived from the read-out image content, and the user, i.e. the radiologist, may refer back to the corresponding image part in order to enable the analyzing algorithm to learn text modules by machine learning, e.g. via heat maps or the like. For example, the text modules can be filled or learned via an appropriate data interface from publicly available databases using finite sets of standardized categories to describe findings within images, such as NIH (see: https://www.nlm.nih.gov/mesh/), as well as commercially available dictionaries, such as SnoMed (see: http://www.snomed.org/snomed-ct). Of course, the text modules can also be pre-defined or learned by offline-interfaces.

Depending on the image analysis, the current section of the report and/or the last user input, several text suggestions may be displayed simultaneously. In this case, the text prediction contains several suggestions that are displayed to the user at the same time, e.g. as a list of individual terms or phrases, wherein the individual suggestions may be displayed in a respective line.

An advantageous effect of the present invention is that the reporting time effort is reduced, especially in comparison to manual reporting, such as dictation, speech recognition or unsupported typing. There are also advantages in view of a background-generated report, as potential corrections to the text due to insufficient image recognition can still be considered during runtime of the text generating unit. Thus, despite the high degree of automation, there is still a constant possibility of intervention for the user. This also reduces the probability of errors in the text content of the report. In addition, if the system is adapted to machine learning, the system can be steadily improved by teaching while the text input that is required anyway for reporting.

In an embodiment, the system, or in particular the text generating unit is further adapted to display an initial text prediction, when the text field is activated but still without written text content.

In this case, the text field may still be empty but activated, e.g. terms or phrases are suggested and displayed that fit either to the determined possible disease and/or with which a the disease descriptive report starts from experience.

Optionally, the system, or in particular the text generating unit, may further be adapted to create or change displayed text prediction in response to an input of a text module part by the user via the input unit.

The displayed text prediction thus reacts continuously to the input of text. The text input and the text prediction may be visually distinguished by visual highlighting.

In an embodiment, the system, or in particular the text generating unit may be further adapted to auto-complete preferably the displayed text prediction to written text content in the text field, when the user confirms the displayed text prediction to be completed by a respective input via the input unit.

Thus, the suggested text content does not have to be completely typed in, but can be completed automatically by means of a short input confirmation, such as a single keystroke.

Optionally, the system, or in particular the text generation unit is further adapted to auto-complete the text prediction in at least one of the following cases:

i) In a first case, the text field is, still or after deleting already written text content, completely unfilled. In response to activating the text field, an initial text prediction is displayed to the user.

The initial text prediction may be, for example, an introductory part of the report that has already been labeled by the system as an appropriate introduction, wherein this may be learned from previous reports, ideally in context with the determined disease.

ii) In a second case, the user may enter at least an initial letter that matches at least one of the pre-defined text modules into the text field. In reaction to entering the letter, and preferably a short confirmation, the matching text module is auto-completed word wise or sentence wise.

Without to come up with an own formulation, whole sentence parts of the report can be auto-completed by a selection from the suggestions and/or a short confirmation.

iii) In a third case, the user enters at least one recognized initial word that matches at least one of the pre-defined text modules, wherein, in reaction to entering the word, the matching text module is auto-completed paragraph wise.

This can also auto-complete whole paragraphs by a selection from the suggestions and/or a short confirmation.

In an embodiment, the text prediction contains at least one text module labeled with a computational identifier that is associated with at least one class of images and wherein the image content is computational associated to the respective class of images.

The association between a given label and the corresponding class of images can be learned or learned from example images previously labeled according to previous or current reporting workflows. For example, the system can also use a Convolutional Neural Network (CNN) for the classification of the image, wherein such classification may, for example, distinguish between normal chest X-Ray images and chest X-Ray images indicative with cardiomegaly. Based on the prediction, respectively its probability, the system may derive the suggestions for terms and/or text modules. In further execution, the system may learn from the user input, so that a deviation from the displayed suggestions, which were initially displayed due to a high probability initially computed, by one or more user corrections, i.e. the selection or input of deviating proposed terns and/or text modules, changes the selection and/or display of the probability. Through this learning process, the text suggestions made for one and the same analyzed image may change over time. As a result, the association between a given label and the corresponding class of images may be learned from user input.

Optionally, the text prediction may contain a display portion indicating the probability that the suggested text module matches the read-out image content and/or the determined possible disease.

For example, the text prediction may be displayed as a list with lines from which the individual suggestions can be selected line by line, with each suggestion also being given the probability in percent. Ideally, when displayed, the rows are sorted by probability, which is computed in background by the system. The probability indicator may be arranged before or after the display of the text suggestion. This may also show the user that in the present automatic image processing several possible diagnoses may be considered and, therefore, a more accurate analysis by human expertise may be appropriate in this case. If the system is capable for machine learning, a single or repeated preference for a less or more likely text suggestion may cause the system taking a different probability score in the future. Of course, there may also be feedback to the image analysis unit in order to also adapt its results to the user's selection.

In an embodiment, the text prediction contains a text module naming and/or describing the applied medical imaging method.

When the one or more images are loaded into and/or processed in the system, information by which imaging method and/or in which conditions the images where taken may also be transmitted. This information can then be suggested as text prediction to the user.

Optionally, the system, in particular the image analyzing unit may further be adapted to analyze the image quality of the provided image data, and in case of image quality deemed to be equivocal and/or inadequate, the text prediction contains text modules at least containing a disclaimer and/or a suggestion for an additional or alternative diagnostic method or examination to be applied.

Thus, the radiologist may point out that with the imaging method used, no clear diagnosis has been possible. Or, it is noted that further studies are recommended for confirmation or clarification.

In an embodiment, the system may further comprise a learning unit adapted to change and/or expand the pre-defined set of text modules in response to a user input via the input unit.

The learning unit may in particular be adapted to functionally adjust each of the above-described system units by appropriate machine learning algorithms, in particular by a feedback to or by changing the associations between the contents of these system units. The system can thus respond continuously to the text input and adjust its text suggestions, taking into account at least the typed letters and/or the probability that the respective text module matches the respective image content.

Further, the learning unit may further be adapted to change and/or expand the association, i.e. the mapping, between at least one of the pre-defined text modules and the read-out image content.

As explained above, the system may be capable to machine learning so that a single or repeated preference for a less or more likely text suggestion may cause the system to an extended or revised association or to remove the association between the respective pre-defined text module and the respective read-out image content. Thus, the user can adjust or teach the system in terms of image content recognition and/or text prediction quality during text input without complicated user menu navigation.

A second aspect of the present invention provides a method for computer-aided preparing a diagnosis report based on medical image data provided by the above-mentioned medical imaging techniques. The method can preferably be carried out as a (part of a) computer program, in particular by means of a processing or computing unit, such as a microprocessor.

The method comprises the following steps:
 Reading out of at least image content from the provided image data.
This method step may comprise electronically processing and/or analyzing the images by means of computer-aided image processing, wherein handcrafted image analysis features or deep learning algorithms can be used.
 Associating the read-out image content to a pre-defined class of images that is computational associated to at least one particular medical- or report-relevant characteristic.
During or after reading out the image content, the system may analyze and classify it. In this context, the system may determine whether at least one characteristic derived from the image content at least match to one or more characteristics that are assigned to a class of images. Of course, such a characteristic can also be assigned to several classes. Likewise, several classes of a property can be assigned. The assignments can also be changed or adapted by the above-mentioned learning unit during runtime or typing the report.
 Displaying text prediction to a user preparing the report on a display, when the user at least activates a text field shown on the display, wherein the text prediction at least contains a pre-defined text module labeled with a computational identifier that is associated to the pre-defined class of images.

However, the image classes are not only assigned to characteristics of the image content, but also to a label and/or computational identifier of a text module, whereby the text module name or describe the characteristics or findings derived from the image content, such as detected abnormalities or complete diagnoses, etc.

In an embodiment, the text module of the displayed text prediction may be changed or auto-completed into written text that is then shown in the text field and/or non-volatile stored for preparing the diagnosis report, in reaction to an input of the user via a input unit.

For example, an initial letter changed during typing may cause the suggested text module to change. Accordingly, the text suggestions can change continuously with the input of additional letters or spaces, at least until there is no more agreement with given text modules.

According to a third aspect, a computer program element is provided for controlling the report preparation system according to the first aspect which, when being executed by a processing unit, is adapted to perform at least the method steps of the second aspect.

According to a fourth aspect, there is provided a computer readable medium having stored the computer program element of the third aspect.

It shall be understood that the system, the method and the computer program have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
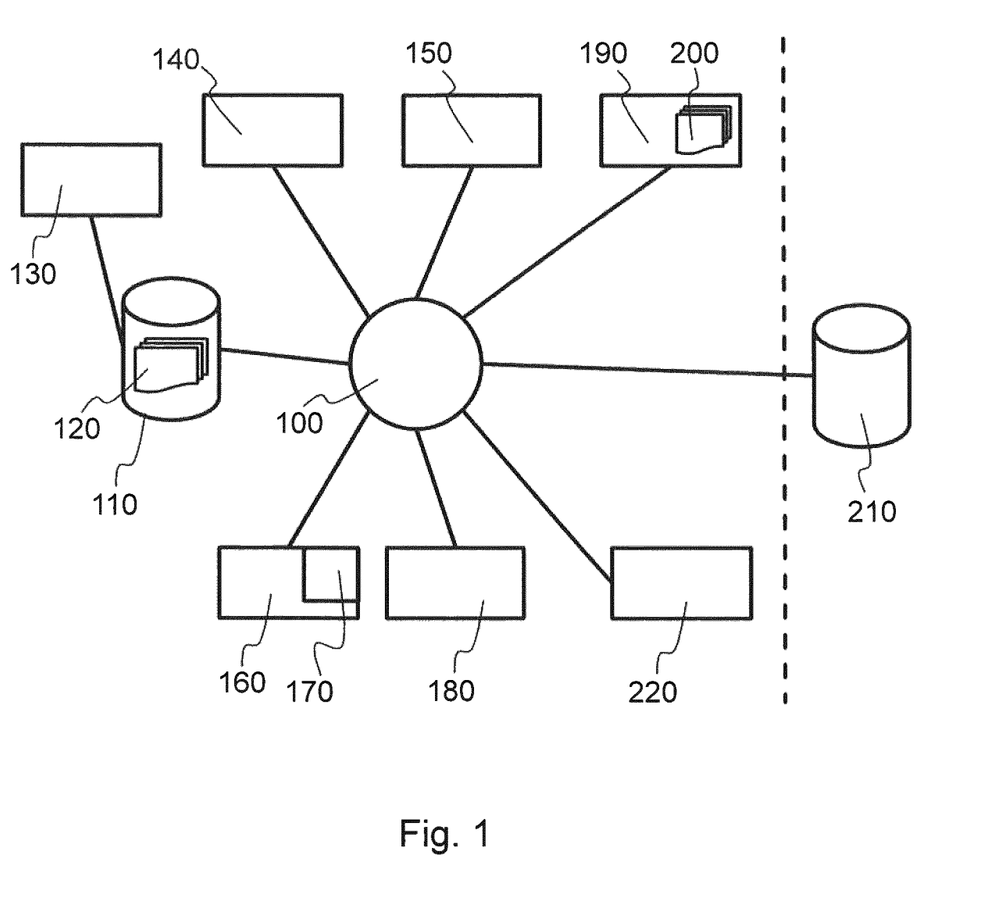
FIG. 1 shows schematically and exemplarily an embodiment of a system for computer-aided diagnosis report preparation based on medical image data provided by medical imaging according to the first aspect.

FIG. 1 shows schematically and exemplarily an embodiment of a system 100 for computer-aided diagnosis report preparation based on medical image data provided by medical imaging. In particular, the system 100 serves to prepare or formulate a report of findings, i.e. the actual text-based reporting, by a user (not shown), such as a radiologist. In this embodiment, the system 100 mainly includes software components, wherein it is implemented by hardware means of a personal computer having a processing unit (not shown) and possibly a server having also a processing unit (not shown). The personal computer can also be a portable computer, such as a tablet or the like. The functional or software components of the system 100 are provided, for example, as a computer program element stored on a computer-readable medium.

First, the system 100 itself or e.g. an healthcare or radiological management system (not shown), such as the Philips' PACS, in which the system 100 is embedded comprises an optional database 110, e.g. implemented on a server, in which previously created images 120 from a medical imaging device 130, such as an X-Ray detector, with an assignment to a patient are stored. The database 110 is connected, for example, via a data network to the system 100 or individual system units described below. Although system units of the system 100 are described below as individual units, they may share common hardware components. Accordingly, they are mainly distinguished functionally from each other.

Further, the system 100 comprises an image processing unit 140 that is adapted to electronically read out at least image content from the provided images 120. In this embodiment, the image processing unit 140 uses a graphics processor and comprises image processing program code. As a result, image processing is possible, at least to the extent that the relevant image content is detected in the image material. In addition, for example, metadata can also be read out. To process the respective image 120, the system 100 is configured to load the images 120 from the database 110 via the data network.

The system 100 further includes an image analyzing unit 150 that is adapted to analyze the read-out image content based on pre-defined or trained characteristics and to derive analysis results. The image analyzing unit 150 in this embodiment uses the same hardware component, i.e. the graphics processor, as the image processing unit 140 above and is thus distinguished mainly in functional terms. A common technique for analyzing the images 120 is machine recognition of specific characteristics, features and conditions in the image content. Since such an analyzing technique is generally known from the above-mentioned prior art, especially from US 2016/0350919 A1, a more detailed description is omitted here.

Furthermore, the system 100 comprises a display device 160 having at least one text field 170 for displaying written text to the user. In this embodiment, the display device 160 comprises a computer monitor that displays a graphical user interface, with the text field 170, among other display and/or text fields (see FIG. 3, being integral part of the graphical user interface. In addition to the hardware computer monitor, the display device 160 comprises a corresponding computer interface.

The system 100 further includes an input unit 180 for interacting with the user to at least activate the text field 170. In this embodiment, the input unit 180 comprises a computer keyboard and a computer mouse, in addition to a corresponding computer interface.

Further, the system 100 comprises a text generating unit 190 that is adapted to provide text prediction to the user on the display device 160, at least when the user activates the text field 170 via the input unit 180, wherein the text prediction is selected from a pre-defined set of text modules 200 that are associated to the analysis result of the image analyzing unit 150.

To predefine the text modules 200, the system 100 is optionally connected to a (external) public database 210 that contains a number of medical vocabularies with a finite set of standardized categories to describe findings within images, such as the images 120, in text form. Prominent examples for such a database 210 include terminologies proposed e.g. by the NIH (see: https://www.nlm.nih.gov/mesh/) as well as commercially available dictionaries such as SnoMed (see: http://www.snomed.org/snomed-ct). It is noted that the text modules 200 can also be learned or predefined offline, i.e. within the system 100, e.g. through databases of the healthcare or radiological management system or individually by the user.

The system 100 also comprises a learning unit 220 that is at least adapted to change and/or expand the pre-defined set of text modules 200 in response to a user input via the input unit 180. It is noted that also other of the system units described above can be taught by the learning unit 220.

In the following, the functions of some of the system units above will now be described in more detail.

Figure 2:
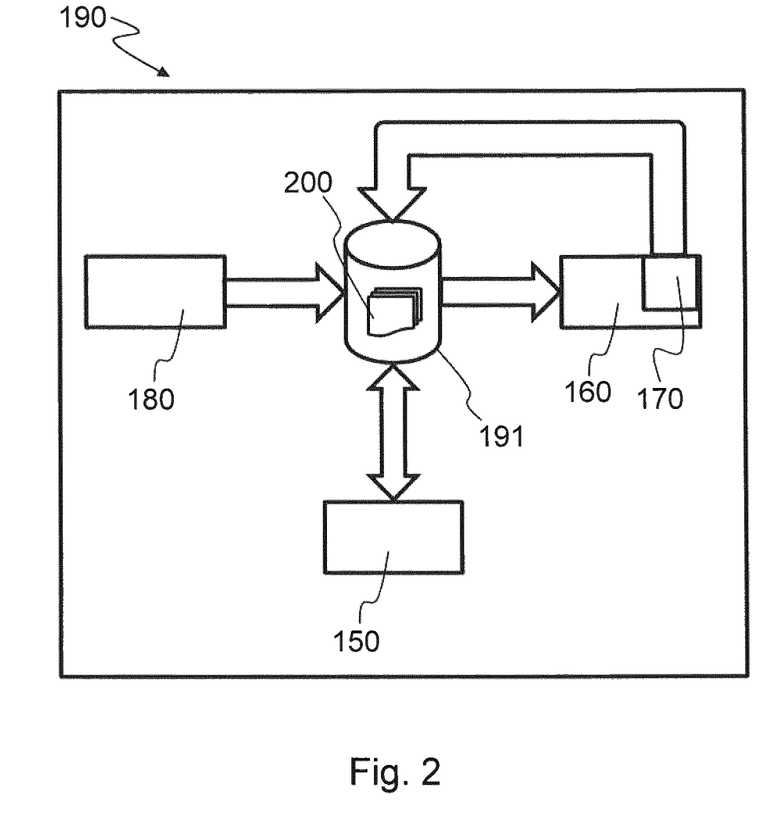
FIG. 2 shows schematically and exemplarily an embodiment of a text generating unit according to the first aspect.
Figure 3:
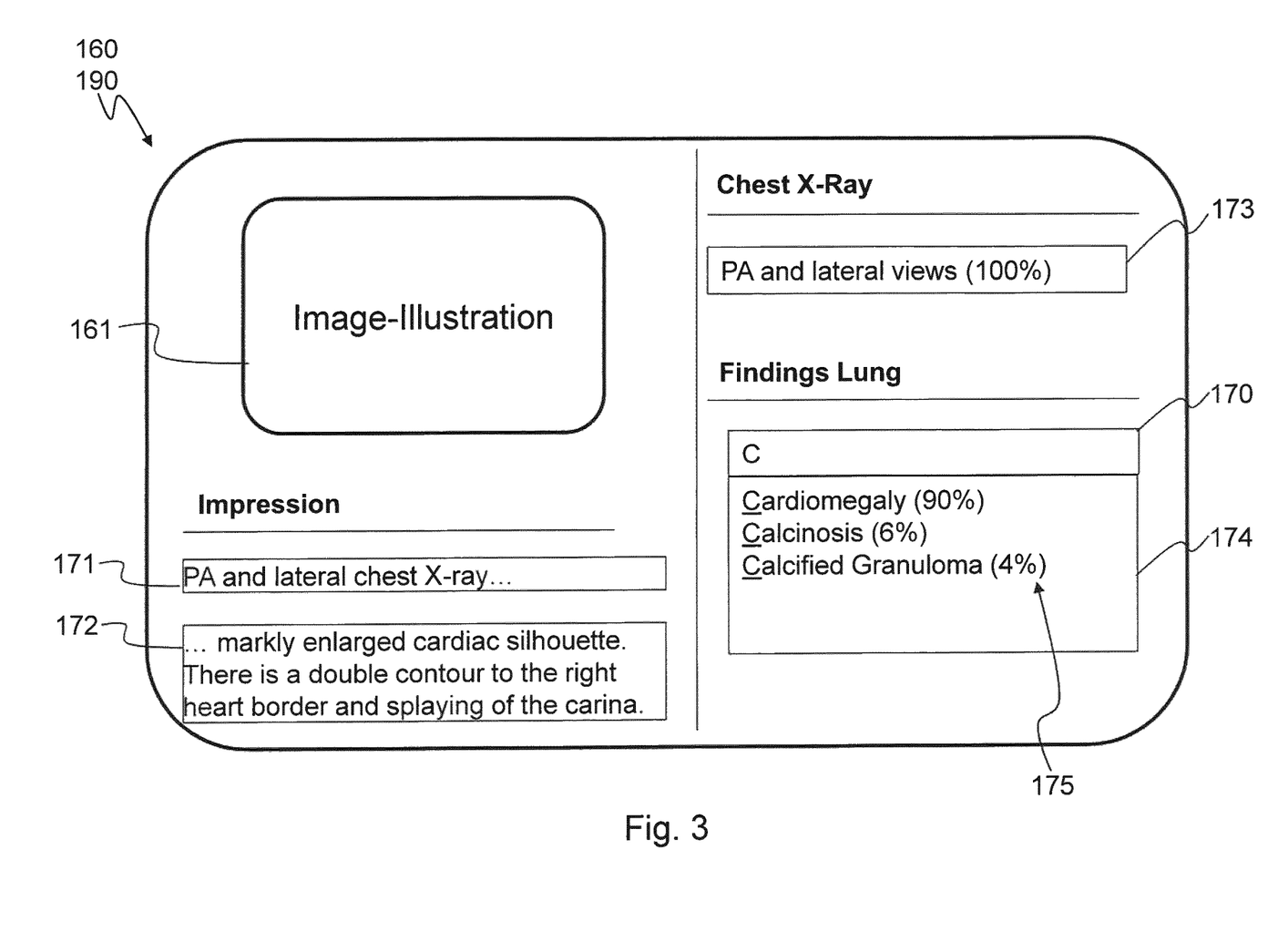
FIG. 3 shows schematically and exemplarily a display unit that displays a text prediction.

First, with reference to FIGS. 2 and 3, the functions of the text generating unit 190 are described. Accordingly, as indicated in FIG. 2, the text generating unit 190 is generally configured to generate text prediction in form of a text output, i.e. word or sentence suggestions, based on a specific selection of the text modules 200 in the text field 170 of the display unit 160 in response to a user action on the input unit 180. Thereby, the text generating unit 190 also takes into account the current status of the text field 170. For this purpose, the text generating unit 190 has several direct or indirect, for example via hardware drivers or software modules, software interfaces to at least the display unit 160, the input unit 180, the image analyzing unit 150 and to a storage unit 191 in which the text modules 200 are stored. Essentially, two different current states of the text field 170 can be distinguished, namely, that the text field 170 is still completely empty but activated by e.g. a mouse click via the input unit 180, and that text has already been entered into the activated text field 170. The situational and context sensitive selection of one or more of the text modules 200 to be displayed in the text field 170 is based on a prior association between the analysis result of the image analyzing unit 150 and the text modules 200, as described in more detail below. Because depending on the image content identified during the image analysis, the selection of text modules 200 changes. As a result, during operation of the text generating unit 190, the generated text prediction contains an initial text prediction related to the image content, when the text field 170 is activated but empty, or text prediction is changed in response to an input of a text module part by the user via the input unit 180.

Furthermore, the text generating unit 190 is further configured to auto-complete the displayed text prediction to written text content in the text field 170, when the user confirms the displayed text prediction to be completed by a respective input via the input unit. In the simplest case, the confirmation is a single command confirmation by pressing a respective key of the keyboard. Also in auto completion the following cases can be distinguished:

1. The text field 170 is, still or after deleting already written text content, completely unfilled. In this case, initial text prediction, e.g. a medical term describing the findings due to analyzing the image content by the image analyzing unit 150 is displayed, when the user has activated the text field 170, as described above. Upon confirmation by the user, the displayed text is then written to the text field 170.

2. The user enters at least an initial letter that matches at least one of the pre-defined text modules 200 into the text field 170. Either in reaction to entering the letter or by the additional confirmation, the matching text module 200 is auto-completed word wise or sentence wise.

3. The user enters at least one recognized initial word that matches at least one of the pre-defined text modules 200. In reaction to entering the word and/or the additional confirmation, the matching text module 200 is auto-completed paragraph wise.

With reference to FIG. 3, the text prediction of the text generating unit 190 can be described in more detail. It shows an exemplary embodiment of the display unit 160 with an input mask for the report to be created, the display unit 160 comprising the text field 170 as explained above, a graphic field 161 and further text fields 171, 172, 173. It is noted that the functionality of the further text fields is identical to the text field 170. These text fields 170 to 173 are assigned to specific sections of the report to be created and accordingly be provided, for example, for information on the imaging method used, the view of the image 120, the image quality achieved, etc. On the basis of this assignment, the text generating unit 190 then makes a further preselection of the text modules 200 to be displayed when the respective text field is activated and/or filled.

The graphic field 161 shows one image of the images 120 which were prior analyzed by the analyzing unit 150 and on the basis of which the selection out from the text modules 200 for displaying as suggestions of text prediction was made. In this example, text fields 171, 172 and 173 have already been filled with text, which can now be explained using the example of the still unfilled text field 170. The user has clicked on the text field 170 to activate with the mouse and then written the letter C. As a result, in a pop-up selection field 174, now a list of (only) the text modules 200 are displayed with initial letter C. As can be seen in FIG. 3, in addition to the respective text module 200, a probability of a suitable association of the displayed text module 200 to the analyzed image 120 shown in graphic field 161 is also displayed in a text field section 175 with a percentage. Based on this probability, the displayed selectable text modules 200 are sorted in ascending order. The displayed text modules 200 are arranged individually line by line, wherein also whole sentences are possible. A particular text module 200 of the list can be selected e.g. while typing via the keyboard by using the directional keys to select the text module and confirming by pressing a key, such as the return key. Alternatively, the text module can be selected by mouse. With the selection and confirmation of the text module 200, this text module is auto-completed into written and displayed text in the text field 170, as explained above.

Figure 4:
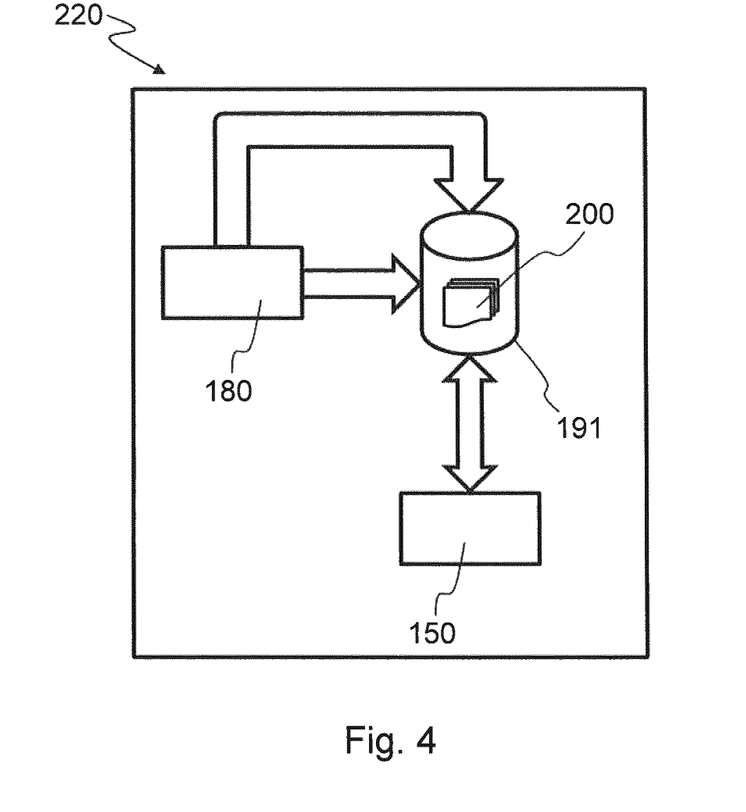
FIG. 4 shows schematically and exemplarily an embodiment of a learning unit according to the first aspect.

With reference to FIG. 4, the learning unit 220 is now described in more detail.

The learning unit 220 has several direct or indirect, for example via hardware drivers or software modules, software interfaces to at least the input unit 180, the image analyzing unit 150 and to the storage unit 191 in which the text modules 200 are stored. It is adapted to recognize text input by the user via the input unit 180 at least when it no longer matches any text module 200 displayed as a suggestion. The system then stores the new term or the new sentence as a new text module to the stored text modules 200 and/or in the case of an existing text module 200, a new assignment to the image content as analyzed by the analyzing unit 150.

Figure 5:
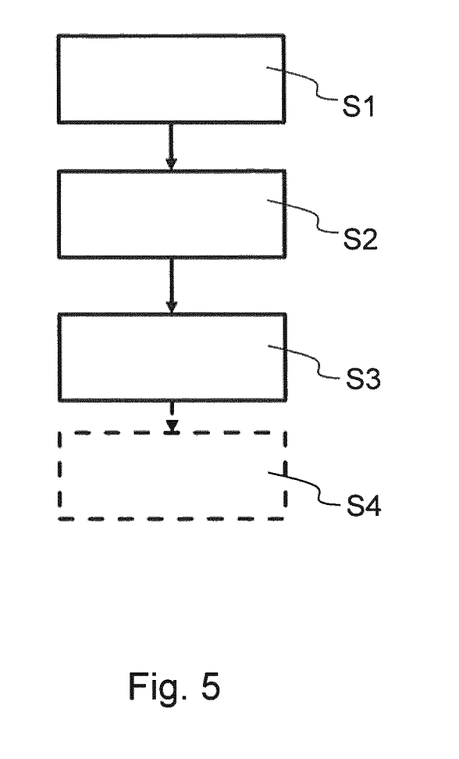
FIG. 5 shows a flow chart of a method according to a second aspect.

In the following, a method according to a second aspect will be described with reference to a flow chart shown in FIG. 5. The method can be used, for example, as a control method for the system 100 described above.

In step S1, at least image content from one or more of the provided images 120 is read-out. This is done via the analyzing unit 150, which optionally also determines the image quality and makes a selection of the text modules 200 from it, e.g. include a disclaimer that indicates the inadequate image quality in the report. In step S2, the read-out image content is associated or assigned to a pre-defined class of images that is computational associated to at least one particular finding which can be e.g. a particular disease. In step S3, text prediction to the user preparing the report is displayed on the display device 160, when the user at least activates the text field 170 shown on the display, wherein the text prediction at least contains one of the pre-defined text modules 200 labeled with a computational identifier that is associated to the pre-defined class of images. In a optional step S4, after selecting one or more of the text modules 200 and/or typing additional (free) text, the report is completed and can be stored, transmitted, printed etc.

It should to be noted that embodiments of the invention are described with reference to different subject-matters. In particular, some embodiments are described with reference to method-type claims, whereas other embodiments are described with reference to device-type claims. However, a person skilled in the art will gather from the above, and the following description that, unless otherwise notified, in addition to any combination of features belonging to one type of subject-matter, also other combinations between features relating to different subject-matters is considered to be disclosed with this application. All features can be combined to provide a synergetic effect that is more than the simple summation of the features.

While the invention has been illustrated and described in detail in the drawings and foregoing description, such illustration and description are to be considered illustrative or exemplary, and not restrictive. The invention is not limited to the disclosed embodiments.

Other variations to the disclosed embodiments can be understood, and effected by those skilled in the art in practicing the claimed invention, from a study of the drawings, the disclosure, and the dependent claims.

In the claims, the word "comprising" does not exclude other elements or steps, and the indefinite article "a" or "an" does not exclude a plurality. A single processor, or other unit, may fulfil the functions of several items recited in the claims. The mere fact that certain measures are recited in mutually different dependent claims does not indicate that a combination of these measures cannot be used to advantage. Any reference signs in the claims should not be construed as limiting the scope.

LIST OF REFERENCE SIGNS

100 System
110 Database
120 Image
130 Medical imaging device
140 Image processing unit
150 Image analyzing unit
160 Display device
161 Graphic field
170 Text field
171 Text field
172 Text field 173 Text field
174 Selection field
175 Text field section
180 Input unit
190 Text generating unit
191 storage unit
200 Text modules
210 External database
220 Learning unit
S1 Method step
S2 Method step
S3 Method step
S4 Method step

The invention claimed is:

1. A system for computer-aided diagnosis report preparation based on medical image data provided by medical imaging, comprising:
 a database storing a plurality of pre-defined text modules, each of the plurality of pre-defined text modules associated with one or more of a plurality of pre-defined classes of medical images;
 an image processing unit configured to read out at least image content from the provided image data;
 an image analyzing unit configured to analyze the read-out image content based on predefined characteristics and to derive an analysis result, wherein the analysis result comprises associating the read-out image content with one or more of the plurality of pre-defined classes of medical images;
 a display device having at least one text field for displaying written text;
 an input unit configured to at least activate the text field; and
 a text generating unit configured to provide text prediction as a visual display of text suggestions that are individually selectable to a user on the display device when the user activates the text field via the input unit, wherein the text prediction is selected from the pre-defined plurality of pre-defined text modules that are associated with the analysis result, the association based on overlap between: (1) the one or more of the plurality of pre-defined classes of medical images associated with the read-out image content and (2) the one or more pre-defined text modules associated with the one or more of the plurality of pre-defined classes of medical images associated with the read-out image content; and
 wherein an initial text prediction is based on the image content and is displayed when the text field is activated without written text content.

2. The system according to claim 1, wherein the displayed text prediction is created, displayed, or created and displayed in response to an input of a text module part via the input unit.

3. The system according to claim 1, wherein the displayed text prediction is autocompleted to written text content in the text field when the displayed text prediction is confirmed to be completed via the input unit.

4. The system according to claim 3, wherein the text prediction is autocompleted in at least one of:
 i) the text field is, still or after deleting already written text content, completely unfilled, wherein, in reaction to activating the text field, initial text prediction is displayed;
 ii) at least an initial letter is entered that matches at least one of the pre-defined text modules into the text field, wherein, in reaction to entering the letter, the matching text module is auto-completed word wise or sentence wise, and
 iii) at least one recognized initial word is entered that matches at least one of the pre-defined text modules, wherein, in reaction to entering the word, the matching text module is auto-completed paragraph wise.

5. The system according to claim 1, wherein the text prediction contains a display portion indicating the probability that the suggested text module matches the read-out image content.

6. The system according to claim 1, wherein the text prediction contains a text module naming, describing or naming and describing the applied medical imaging method.

7. The system according to claim 1, wherein the system is further configured to analyze the image quality of the provided image data, and in case of image quality deemed to be inadequate, the text prediction contains text modules at least containing a disclaimer, a suggestion or a disclaimer and suggestion for an additional or alternative diagnostic method or examination to be applied.

8. The system according to claim 1, comprising a learning unit configured to change, expand or change and expand the pre-defined set of text modules in response to input via the input unit.

9. The system according to claim 8, wherein the learning unit is further configured to change, expand or change and expand the association between at least one of the pre-defined text modules and the read-out image content.

10. The system according to claim 1, wherein the initial text prediction is changed in response to entry of written text content in the text field.

11. The system according to claim 1, wherein the pre-defined set of text modules are learned or predefined offline through databases of a healthcare or radiological management system or individually by the user.

12. The system according to claim 11, wherein the databases contain a number of medical vocabularies with a finite set of standardized categories to describe findings within images in text form.

13. The system according to claim 1, comprising a learning unit configured to recognize user input text when the text no longer matches the pre-defined set of text modules and stores the recognized user input text as a text module.

14. The system according to claim 1, comprising a learning unit configured to recognize user input text when the text no longer matches the pre-defined set of text modules and stores the recognized user input text as a assignment to the image content.

15. The system according to claim 1, wherein the text generating unit is further configured to provide a text prediction for at least one other text field displayed via the display device.

16. The system according to claim 1, further comprising a machine learning algorithm trained to associate, based on training data, analysis results from read-out image content with one or more of the plurality of pre-defined classes of medical images.

17. A method for computer-aided preparation of a diagnosis report based on medical image data provided by medical imaging, comprising:
 storing a plurality of pre-defined text modules, each of the plurality of pre-defined text modules associated with one or more of a plurality of pre-defined classes of medical images;
 reading out at least image content from the provided medical image data;

associating the read-out image content with one or more of the pre-defined classes of medical images, each of the one or more pre-defined classes of medical images being computationally associated with at least one particular finding; and displaying text prediction on a display device when a text field shown on the display device is activated, wherein the text prediction at least contains one or more of the pre-defined text modules, wherein an initial text prediction is displayed when the text field is empty and activated without written text content, and further wherein the text prediction is based on an overlap between: (1) the one or more of the plurality of pre-defined classes of medical images associated with the read-out image content and (2) the one or more pre-defined text modules associated with the one or more of the plurality of pre-defined classes of medical images associated with the read-out image content.

18. The method according to claim 17, wherein, in response to an input of the user via an input unit, the text module of the displayed text prediction is changed or autocompleted into written text that is then shown in the text field, stored for preparing the diagnosis report, or shown in the text field and stored for preparing the diagnosis report.

19. A non-transitory computer-readable medium having executable instructions stored thereon which, when executed by at least one processor, cause the at least one processor to perform a method for computer-aided preparation of a diagnosis report based on medical image data provided by medical imaging, comprising:

storing a plurality of pre-defined text modules, each of the plurality of pre-defined text modules associated with one or more of a plurality of pre-defined classes of medical images;

reading out at least image content from the provided medical image data;

associating the read-out image content with one or more of the pre-defined classes of medical images, each of the one or more pre-defined classes of medical images being computationally associated with at least one particular finding; and displaying text prediction on a display device when a text field shown on the display device is activated, wherein the text prediction at least contains one or more of the pre-defined text modules, wherein an initial text prediction is displayed when the text field is empty and activated without written text content, and further wherein the text prediction is based on an overlap between: (1) the one or more of the plurality of pre-defined classes of medical images associated with the read-out image content and (2) the one or more pre-defined text modules associated with the one or more of the plurality of pre-defined classes of medical images associated with the read-out image content.

* * * * *